US007361179B2

(12) United States Patent
Rousseau et al.

(10) Patent No.: US 7,361,179 B2
(45) Date of Patent: Apr. 22, 2008

(54) STERNAL CLOSURE DEVICE AND METHOD

(75) Inventors: Robert A. Rousseau, Ottsville, PA (US); Kevin S. Weadock, Princeton, NJ (US); Etan S. Chatlynne, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 507 days.

(21) Appl. No.: 10/830,122

(22) Filed: Apr. 22, 2004

(65) Prior Publication Data

US 2005/0240189 A1    Oct. 27, 2005

(51) Int. Cl.
*A61B 17/56*    (2006.01)
(52) U.S. Cl. ....................................... 606/72
(58) Field of Classification Search ............ 606/72–76, 606/78
See application file for complete search history.

(56) References Cited

U.S. PATENT DOCUMENTS

| 309,350 | A | 12/1884 | Hayden |
|---|---|---|---|
| 3,802,438 | A | 4/1974 | Wolvek |
| 4,122,989 | A | 10/1978 | Kapitanov et al. |
| 4,201,215 | A | 5/1980 | Crossett et al. |
| 4,210,148 | A | 7/1980 | Stivala |
| 4,279,248 | A | 7/1981 | Gabbay |
| 4,512,346 | A | 4/1985 | Lemole |
| 4,535,764 | A | 8/1985 | Enert |
| 4,548,202 | A | 10/1985 | Duncan |
| 4,583,541 | A | 4/1986 | Barry |
| 4,730,615 | A | 3/1988 | Sutherland et al. |
| 4,802,477 | A | 2/1989 | Gabbay |
| 4,813,416 | A | 3/1989 | Pollak et al. |
| 4,896,668 | A | 1/1990 | Popoff et al. |
| 5,089,012 | A | 2/1992 | Prou |
| 5,098,433 | A | 3/1992 | Freedland |
| 5,139,498 | A | 8/1992 | Astudillo Ley |
| 5,163,598 | A | 11/1992 | Peters et al. |
| 5,318,566 | A | 6/1994 | Miller |
| 5,330,489 | A | 7/1994 | Green et al. |

(Continued)

FOREIGN PATENT DOCUMENTS

EP    0464480 A    1/1992

(Continued)

OTHER PUBLICATIONS

European Search Report dated Nov. 4, 2005 for corresponding Appln. No. 05252668.

*Primary Examiner*—Eduardo C. Robert
*Assistant Examiner*—Michael J. Araj

(57) ABSTRACT

A device and method for joining a severed sternum is disclosed. The device includes first and second bearing members, a sternum joining member having an axis and first and second ends, the first end connected to the first bearing member, the second bearing member adapted to engage the sternum joining member, and the sternum joining member is adapted to traverse the exposed cancellous surfaces of the sternal portions. The method includes moving the second bearing member along the axis of the sternum joining member toward the first bearing member, with the sternum joining member traversing the cancellous surfaces of both sternal portions, and securing the second bearing member on the axis of the sternum joining member so that the severed sternum is securely closed. A kit including sternal closure devices and other tools for closing a sternotomy is also disclosed.

2 Claims, 13 Drawing Sheets

U.S. PATENT DOCUMENTS

| | | |
|---|---|---|
| 5,356,412 A | 10/1994 | Golds et al. |
| 5,356,417 A | 10/1994 | Golds |
| 5,366,461 A | 11/1994 | Blasnik |
| 5,417,698 A | 5/1995 | Green et al. |
| 5,423,821 A | 6/1995 | Pasque |
| 5,437,685 A | 8/1995 | Blasnik |
| 5,462,542 A | 10/1995 | Alesi, Jr. |
| 5,722,976 A * | 3/1998 | Brown ................. 606/69 |
| 5,830,234 A | 11/1998 | Wojciechowicz et al. |
| 5,849,012 A | 12/1998 | Abboudi |
| 5,893,879 A | 4/1999 | Hirshowitz et al. |
| 5,968,077 A | 10/1999 | Wojciechowicz et al. |
| 5,972,006 A | 10/1999 | Sciaino, Jr. |
| 6,007,538 A | 12/1999 | Levin |
| 6,008,535 A | 12/1999 | Jean et al. |
| 6,033,429 A | 3/2000 | Magovern |
| 6,045,572 A | 4/2000 | Johnson et al. |
| 6,051,007 A | 4/2000 | Hogendijk et al. |
| 6,080,185 A | 6/2000 | Johnson et al. |
| 6,200,318 B1 | 3/2001 | Har-Shai et al. |
| 6,217,580 B1 | 4/2001 | Levin |
| 6,302,899 B1 | 10/2001 | Johnson et al. |
| 6,312,431 B1 | 11/2001 | Asfora |
| 6,358,270 B1 | 3/2002 | Lemer |
| 6,368,342 B1 | 4/2002 | Lemer |
| 6,692,497 B1 | 2/2004 | Toermaelae et al. |
| 6,712,821 B2 * | 3/2004 | Gabbay ................. 606/71 |
| 6,921,401 B2 * | 7/2005 | Lerch et al. ............ 606/72 |
| 7,094,239 B1 * | 8/2006 | Michelson ............. 606/70 |
| 2002/0143336 A1 | 10/2002 | Hearn |
| 2002/0161439 A1 | 10/2002 | Strobel et al. |
| 2002/0165548 A1 | 11/2002 | Jutley |
| 2003/0040746 A1 | 2/2003 | Mitchell et al. |
| 2003/0083694 A1 | 5/2003 | Miller, III |
| 2003/0114856 A1 | 6/2003 | Nathanson et al. |
| 2003/0153947 A1 | 8/2003 | Koseki |

FOREIGN PATENT DOCUMENTS

| | | |
|---|---|---|
| RU | 2199288 C1 | 2/2003 |
| WO | WO 87/01270 A | 3/1987 |
| WO | WO 00/64366 A1 | 11/2000 |
| WO | WO 01/22989 A2 | 4/2001 |
| WO | WO 02/067795 A | 9/2002 |
| WO | WO 2004/028412 A | 4/2004 |

* cited by examiner

STERNAL CLOSURE DEVICE AND METHOD

BACKGROUND OF THE INVENTION

The present invention relates generally to surgical devices for the repair of split portions of tissue, in particular, to surgical devices for closing a severed sternum.

The sternum is an elongated, flattened bone, forming the middle portion of the anterior wall of the thorax. Its upper end supports the clavicles, and its margins articulate with the cartilages of the first seven pairs of ribs. It consists of three parts, named from the neck downward, the manubrium, the body, and the xiphoid process. Its average length in an adult is about 17 cm, and is slightly less in a female adult. The sternum is a composite bone structure with a thin cortical shell surrounding a low-density cancellous core. Cortical bone is ivory-like and is dense in texture without cavities. It is the shell of many bones, surrounding the cancellous bone in the center. Cancellous bone is sponge-like with numerous cavities.

During surgery involving thoracic organs such as the heart, lungs, esophagus and aorta, it may be required to split the sternum to provide sufficient access for the surgeon. A partial or median sternotomy is a procedure by which a saw or other cutting instrument is used to make a midline, longitudinal incision along a portion of, or the entire axial length of the patient's sternum, allowing two opposing sternal halves to be separated laterally. Upon completion of the surgery, the sternum is rejoined and closed.

The two sternal halves are typically closed with stainless steel wire sutures that engage the severed sternal edges in a face-to-face relationship and compress them together while the sternum heals. The wire sutures are wrapped around the sternal halves by passing them through the intercostal spaces adjacent to the sternum. They may also be pierced through both halves of the sternum, particularly near the manubrium. Various piercing and wrapping patterns are used by different surgeons. For example, the wire sutures may be applied in an "X" pattern as viewed from the anterior portion of the sternum, to reduce axial motion of the sternal halves relative to each other. Regardless of the method, the ends of the wire sutures are twisted together to tighten the wire loops to a point where the sternal edges are approximated under tension.

U.S. Pat. No. 3,802,438 discloses sternal closure with wire sutures in conjunction with a splice plate in which the wire sutures are received. Other sternal closure assemblies include one or two metal plates, these plates being provided with rows of openings, through which extend the screws, pins, or metal wire, to bring together the severed portions of the sternum. In U.S. Pat. No. 4,583,541, wire bands are used in concert with an elongated, generally strap-like board, placed at the front of the sternum through which the wires are passed. Knots are then made and the knots then placed within a groove in the board.

Clamps, clasps, bands, and strips have been developed as sternal closure devices. For example, U.S. Pat. No. 4,201,215 discloses the use of a two-piece C-shaped clamp at one side of the sternum, the clamp pieces having hook ends that pass around to the other side of the sternum. Other assemblies completely circle the sternum and employ complex locking mechanisms to effect compression of the two sternal halves together. Representative examples are described in U.S. Pat. Nos. 5,356,417; 5,462,542; and 6,007,538.

There are numerous drawbacks with the use of wire sutures. For example, surgeons typically do not have means for ensuring that the tension in one wire suture is the same as the tension in another. Another drawback is that excessive twisting of the wire suture during tensioning can also result in hardening of the wire suture and breakage during the sternal closure procedure or after the surgical procedure. After being twisted together, the excess wire suture must be cut away, leaving sharp ends which may be palpable through the skin, painful and cosmetically undesirable. Surgeons may also be concerned about the potential for the wire suture to injure small blood vessels or nerves near the underside of the sternum. Moreover, the use of devices such as clamps, etc., that completely wrap around the sternum may irritate or damage tissue and vital structures such as blood vessels, particularly on the underside of the sternum.

Another drawback with the use of wire suture is that the amount of force necessary to close the sternum may cause the wire suture, which has a very small load-bearing surface, to cut through the cortical and cancellous portions of sternum. Additionally, the wire suture may cut through the cortical and cancellous portions of the sternum after sternal closure has been achieved, particularly when the wire sutures are subjected to intermittent severe loading due to coughing and other movements of the patient. These loads are transmitted primarily through the wire suture to the cortical component of the sternum. In some cases, this results in a loosening of a wrapped wire suture or an enlargement of the pierced holes in the sternum when the wire suture is pierced through the sternal halves. This loosening of the wrapped wire suture or the enlargement of the holes enables motion of the two halves of the sternum relative to each other. This motion may allow the sternal halves to separate and inhibit proper wound healing. In some cases, this separation may further allow opportunistic organisms to invade the tissue and cause an infection. Such an infection in the sternum is associated with significant morbidity and sometimes death. None of the devices described above that utilize wire sutures offers protection from shear loading and the resultant axial motion of the sternal halves.

Ideally, the device chosen to close a severed sternum must be simple in design, safe and easy to implant and remove, and should not damage adjacent tissue. It should not cause irritation to the patient or be cosmetically unacceptable. It must also be able to provide a secure sternal closure when challenged with post-surgical movement by the patient, particularly coughing. It is therefore an object of the present invention to provide a device and method that overcome the disadvantages of those known in the art.

SUMMARY OF THE INVENTION

The invention is generally directed to a device and method for closing a severed sternum. One particular aspect of the invention is directed to a device for joining first and second portions of a severed sternum, each portion having cortical and cancellous surfaces, the device comprising first and second bearing members; a sternum joining member comprising an axis, a first end, and a second end; the first end connected to the first bearing member; the second bearing member adapted to engage the sternum joining member, and the sternum joining member is adapted to traverse the cancellous surfaces of the first and second sternal portions.

Another aspect of the invention is directed to a method for closing a severed sternum having first and second portions, each portion having cortical and cancellous surfaces, comprising the steps of attaching a first bearing member to the first sternal portion; attaching a second bearing member to the second sternal portion; providing a sternum joining member having a first end, a second end, and an axis between the first end and second end; connecting the first bearing member to the first end of the sternum joining member; and attaching the second end of the sternum joining member to the second bearing member; wherein the sternum joining member traverses the cancellous surfaces of the first and second sternal portions.

Yet another aspect of the invention is directed to a kit for closing a severed sternum, the kit comprising at least one of the sternal closure devices mentioned above, means for creating at least one hole in the sternum, a guide, an introducer, a grasping device, and moving means for moving the second bearing member along the axis of the sternum joining member towards the first bearing member, the moving means further comprising means for measuring tension in the sternum joining member.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1A:
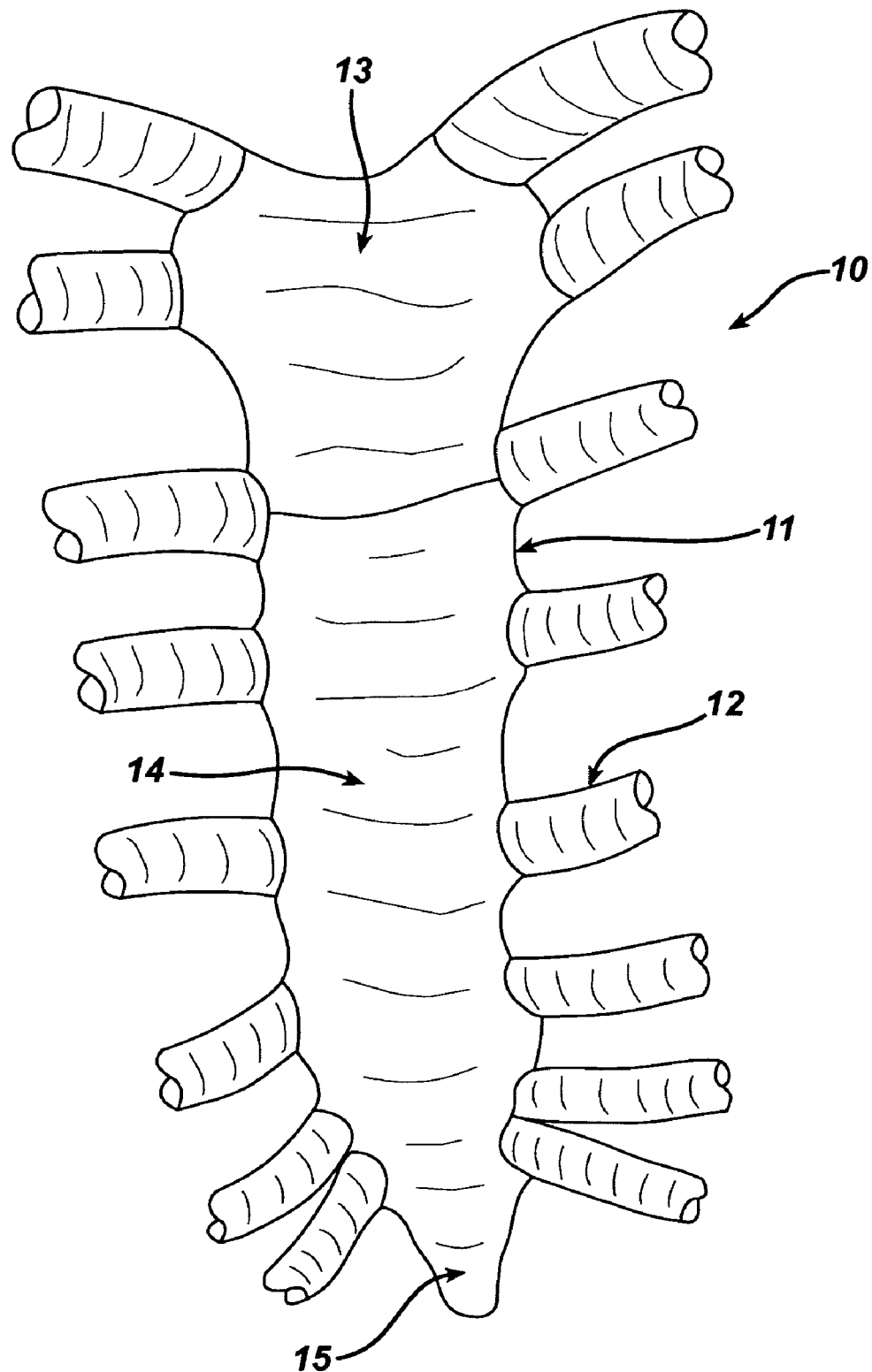
FIG. 1A illustrates a sternum prior to being opened with a surgical instrument.
Figure 1B:
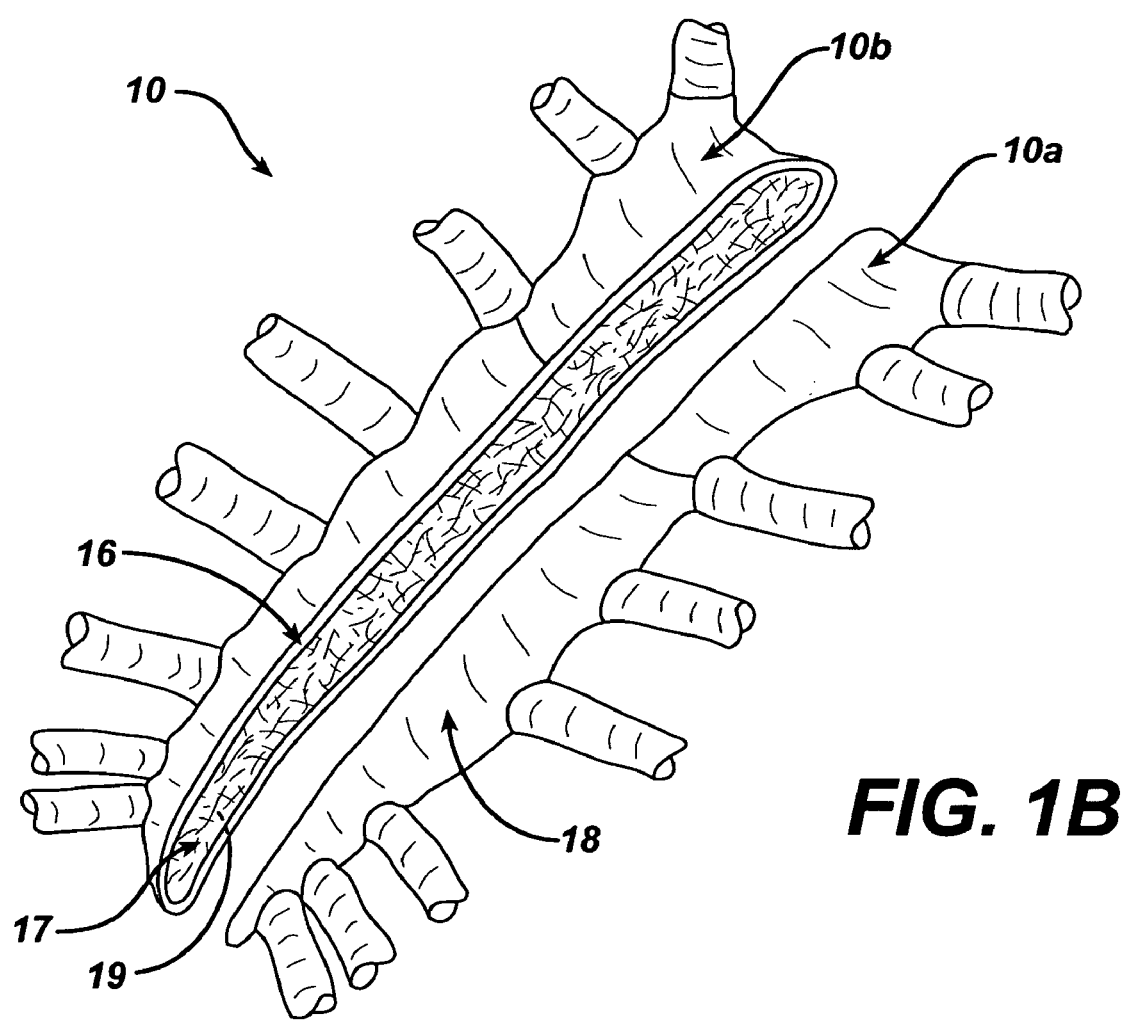
FIG. 1B illustrates a sectional view of the sternum after being opened with a surgical instrument. The cortical and cancellous surfaces of the sternum are identified.

The device will now be described by way of example only and not to limit the spirit or scope of the present invention. Referring now to FIG. 1A, a human sternum generally referred to by reference numeral 10 is shown along with intercostal spaces 11, ribs 12 near the attachment point to the sternum, manubrium 13, body 14, and xyphoid process 15. FIG. 1B illustrates the sternum 10 after a median sternotomy has been performed. The sternum 10 is split into a first portion 10a and a second portion 10b. The cortical surface 16 and cancellous surface 17 of a portion of the sternal incision margin is also illustrated. Also illustrated are the anterior surface 18 and posterior surface 19 of the sternum 10.

Figure 2:
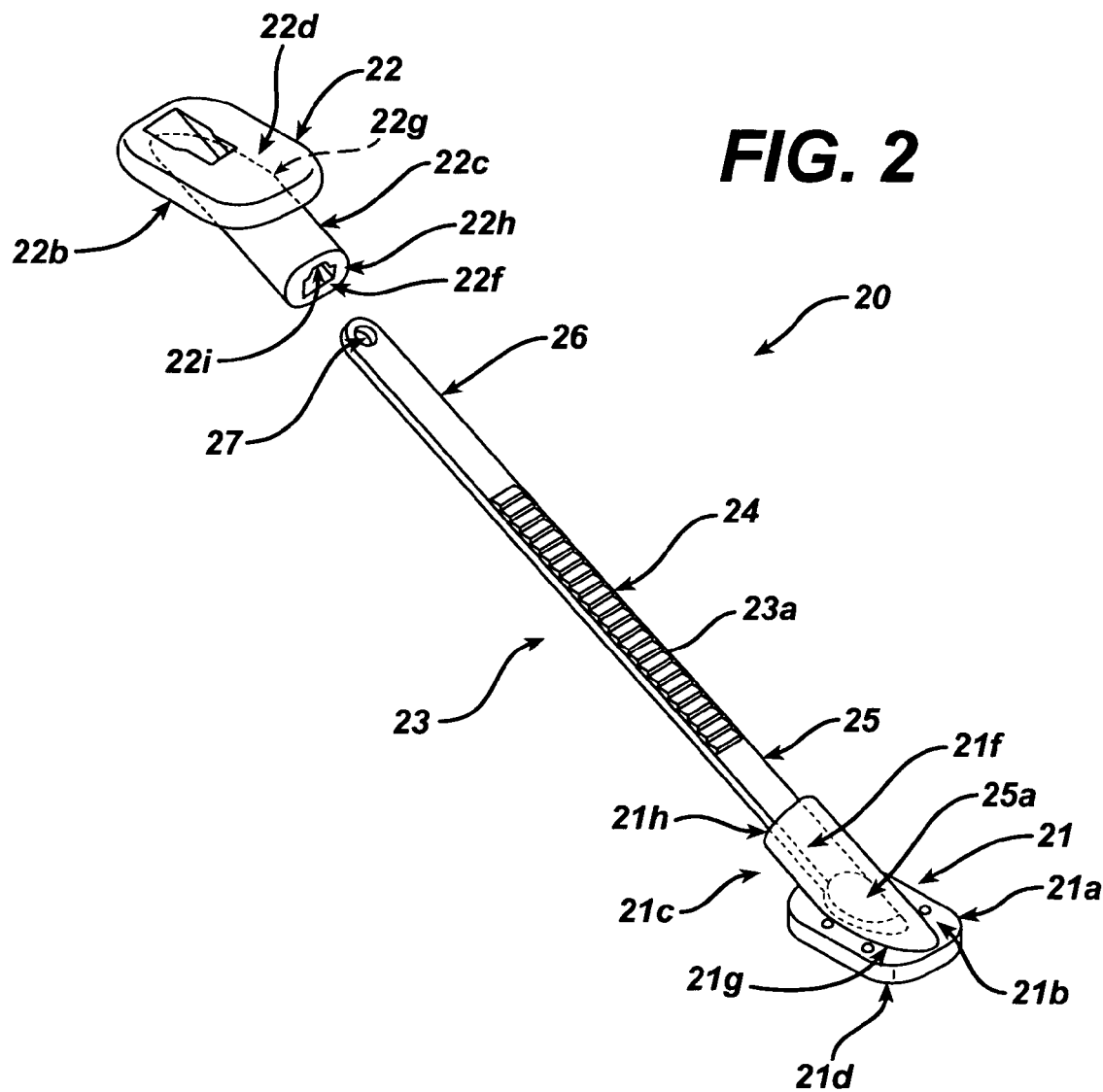
FIG. 2 illustrates an isometric view of one embodiment of the sternal closure device.

Referring now to FIG. 2, the sternal closure device is generally referred to by reference numeral 20 and includes a first bearing member 21, a second bearing member 22, and a sternum joining member 23 having an axis 24, a first end 25 and a second end 26. The first bearing member 21 may have a sternum contacting side 21b, a surface that faces away from the sternum 21d, a sidewall 21a, optionally a protrusion 21c having a first end 21g and second end 21h, where the first end 21g of the protrusion 21c may be attached to the sternum contacting side 21b, the second end 21h of the protrusion 21c extending away from the sternum contacting side 21b. The second bearing member 22 may have a sternum contacting side 22b, a surface that faces away from the sternum 22d, optionally a protrusion 22c having a first end 22g and second end 22h, where the first end 22g of the protrusion 22c may be attached to the sternum contacting side 22b, the second end 22h of the protrusion 22c extending away from the sternum contacting side 22b.

The shape of the first 21 and second bearing member 22 may be relatively flat for when the first bearing member 21 is attached to the anterior 18 or posterior surface 19 of the sternum 10. When the device is used on the anterior 18 and posterior surface 19 of the sternum 10, the sternum contacting sides 21b and 22b of the first 21 and second bearing members 22 may be at an oblique angle with respect to the axis 24 of the sternum joining member 23. The sternum contacting side 21b may also have rasps thereon that extend away from the sternum contacting side 21b to provide a secure engagement of the sternum contacting side 21b with the cortical surface 16 of the sternum 10.

The first end 25 of the sternum joining member 23 may be rigidly, integrally, slidably or releasably attached to the sternum contacting side 21b or optionally the protrusion 21c of the first bearing member 21, or in a manner that allows some rotation of the first bearing member 21 about the axis 24. For example, the protrusion 21c may have a lumen 21f that the first end 25 of the sternum joining member 23 is passed through. The first end 25 of the sternum joining member 23 may be flared 25a so as to prevent being pulled out of the lumen 21f when tension is applied during closure. Alternatively, the first end 25 of the sternum joining member 23 may be abutted against the sternum contacting side 21b of the first bearing member 21 while still allowing rotation thereon. This will allow for minor adjustments of the position of the first bearing member 21 on the sternum 10. Alternatively, the protrusion 21c on the first bearing member 21 may be rigidly fixed to the first end 25 of the sternum joining member 23 by welding or having the first bearing member 21 and entire sternum joining member 23 fabricated as a single piece through casting, molding, machining or other means known to those skilled in the art of fabricating small pans.

The second bearing member 22 may be slidably or releasably engaged with the axis 24 of the sternum joining member 23. For example, the second end 26 of the sternum joining member 23 may be adapted to engage a lumen 22f in the protrusion 22c of the second bearing member 22. The sternum joining member 23 may have means disposed along its axis 24 that facilitate movement of the second bearing member 22 towards the first bearing member 21. As illustrated in FIG. 2, the means may be a ratcheted surface 23a along at least one surface of the sternum joining member 23 between the first bearing member 21 and second bearing member 22, and a surface in the lumen 22f of the second bearing member 22 that allows movement of the second bearing member 22 along the axis 24 of the sternum joining member 23 only towards the first bearing member 21, such as a counter ratcheting surface 22i. The advancing means may also function as a securing means to lock the second bearing member 22 on the axis 24 once a desired tension has been reached in the sternum joining member 23. Alternative securing means can be disposed on the axis 24 of the sternum joining member 23, within the lumen 22f of the second bearing member 22, or both. Such means may include, but is not limited to, a wedge lock or a non-reversing cinch loop on the second bearing bearing member 22, or a barbed surface or perforated surface on the sternum joining member 23. Other conventional securing means may also be employed. Optionally, the second end 26 of the sternum joining member 23 may be secured to the protrusion 22c of the second bearing member 22 by crimping or welding.

The second end 26 of the sternum joining member 23 may include a hole 27 that can be used, along with a grasping instrument or hooking device, to help draw the second end 26 through the cortical 16 and cancellous portions 17 of the sternum 10. In alternative embodiments, the second end 26 may have a hook, flared end, or indentation that would also facilitate passing it through the sternum 10. The axis 24 of the sternum joining member 23 is adapted to traverse the cancellous surface 17 of the first 10a and second portion 10b of the severed sternum, obliquely in one or more directions or perpendicularly traversing the sternal incision margins created when the sternum was severed into two portions. The adaptation is made by having sufficiently long axis 24 with a diameter or cross-sectional area small enough to avoid undue interruption of the cancellous bone within the sternum. It should also be large enough to afford sufficient sternum joining strength. Preferably, the length of the axis 24 is 1-30 cm. The excess portion of the axis 24 can be removed at the end of the procedure. The diameter of the axis 24 is preferably between 1 mm-5 mm. If an axis 24 with a non-circular cross-section is utilized, the preferred cross-sectional area would be 1-25 $mm^2$.

Figure 3A:
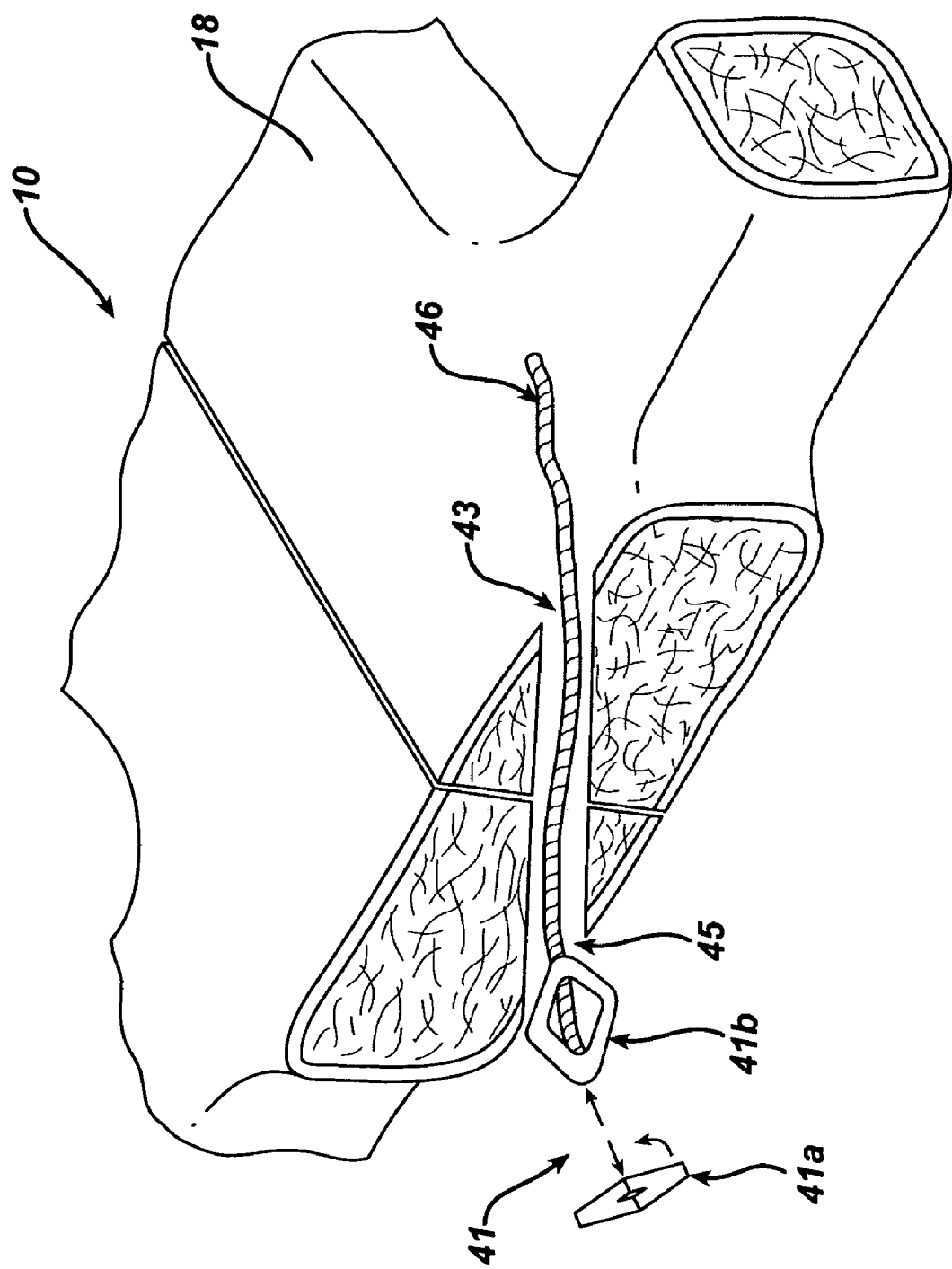
FIG. 3A illustrates the use of a collapsible and expandable anchor as the first bearing member.

Referring now to FIGS. 3A-3E, alternative embodiments are illustrated. FIG. 3A illustrates the use of a collapsible and expandable anchor as the first bearing member 41. In these embodiments, the first bearing member and sternum joining member may be inserted from the anterior surface 18 of the sternum 10. The first bearing member 41, attached to the first end 45 of the sternum joining member 43, is inserted into the holes created in each of the sternal portions in a collapsed position 41b. Once in the desired location, the sternum joining member is pulled so that the first bearing member 41 abuts the sternum surface and opens to form a low-profile anchor 41a. A second bearing member (not shown) can then be applied to the second end 46 of the sternum joining member 43 in a manner similar to that described in FIG. 2.

Figure 3B:
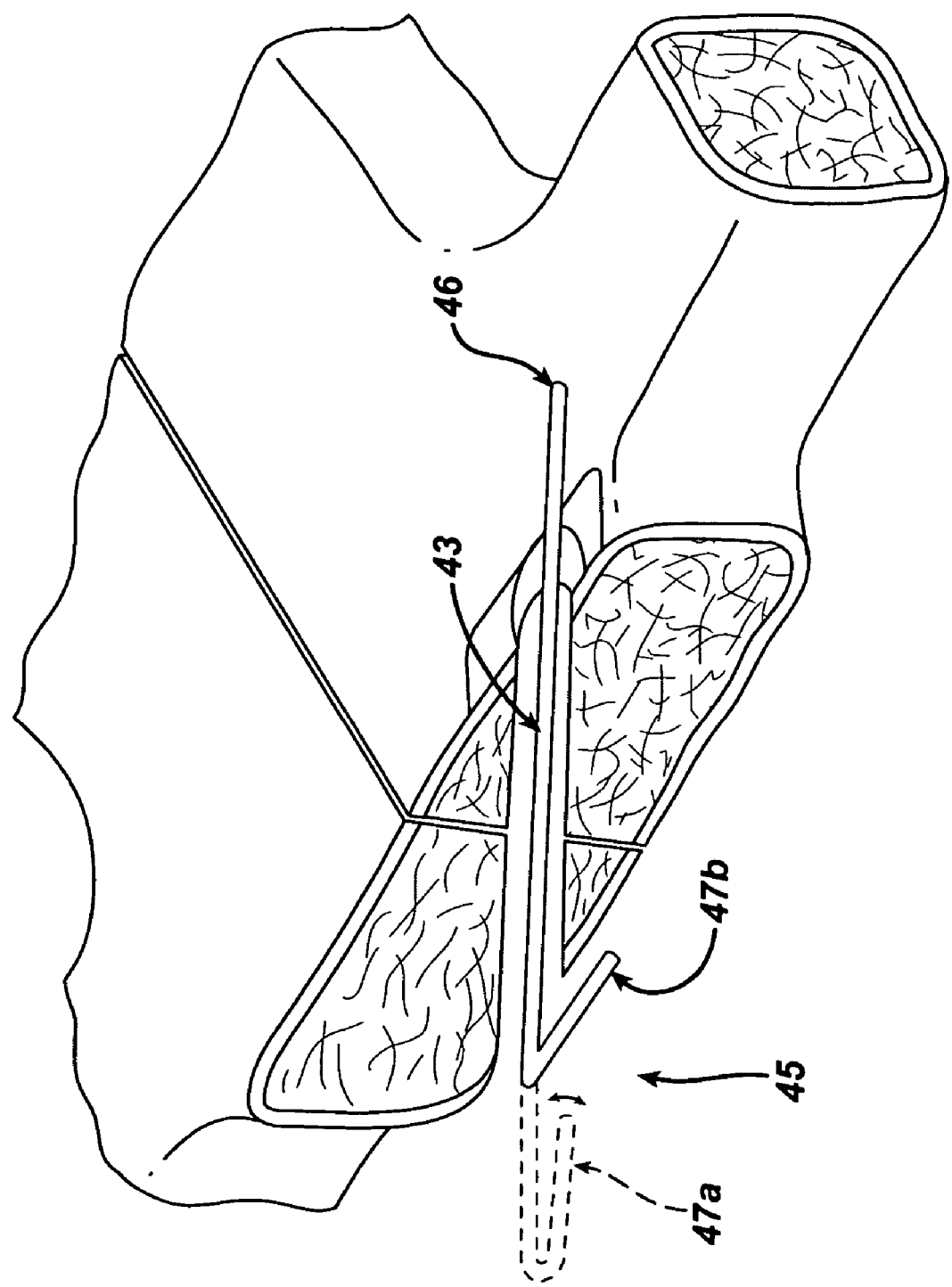
FIG. 3B illustrates a the use of an expandable anchor comprised of a superelastic material such as nitinol to serve as the first bearing member.
Figure 3C:
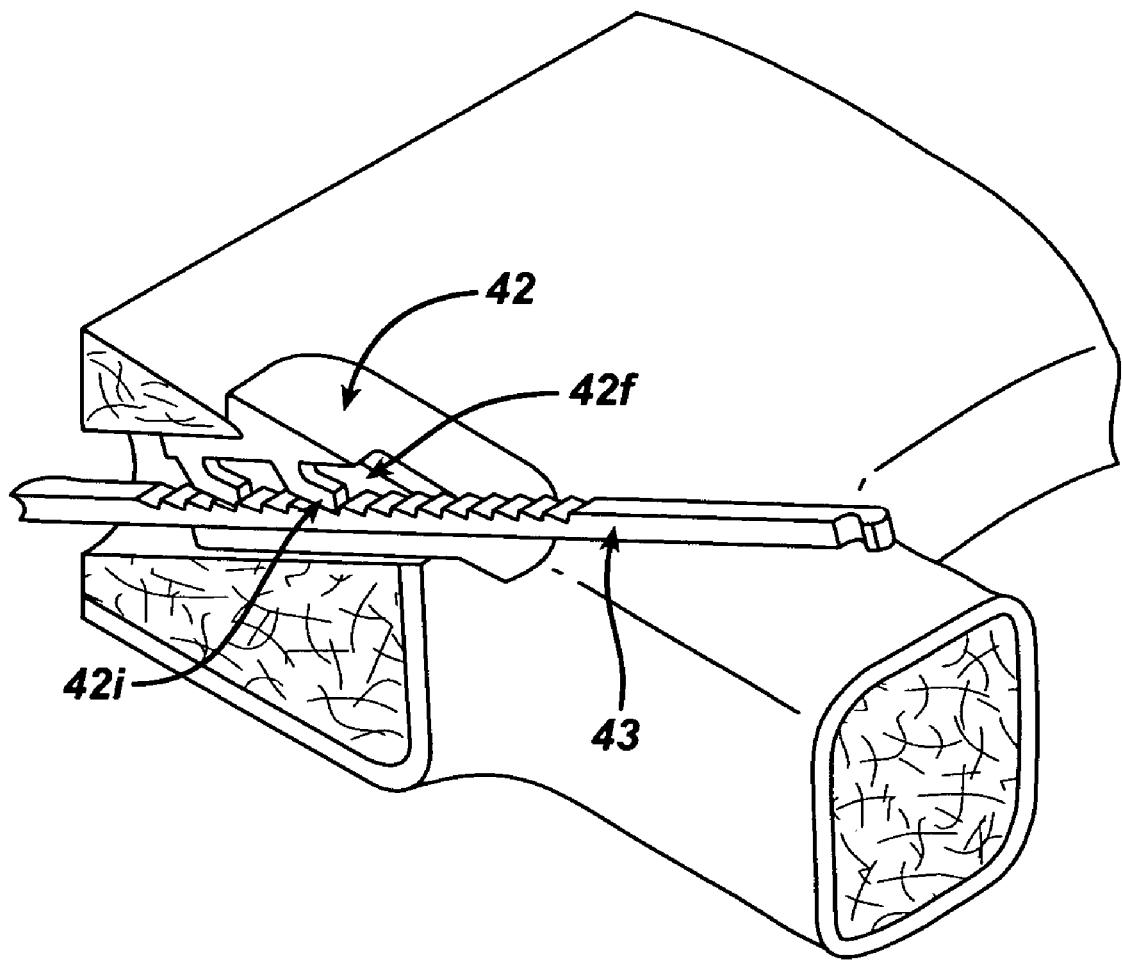
FIG. 3C illustrates the wedge lock.

FIG. 3B illustrates a first bearing member that serves as an expandable anchor in that it is comprised of a superelastic material such as nitinol. The first bearing member has a flange that is compressed when in its first collapsed configuration 47a. This configuration is useful for passing the bearing member through the holes created in the sternal halves. Upon exiting the sternum, the superelastic bearing member changes to a second low profile configuration 47b that cannot be pulled through the hole in the sternum. A second bearing member can then be applied to the second end 46 of the sternum joining member 43 in a manner similar to that described above. As shown in FIG. 3C, the lumen 42f of the second bearing member 42 may have a wedge lock 42i for securely engaging the sternum joining member 43.

Figure 3D:
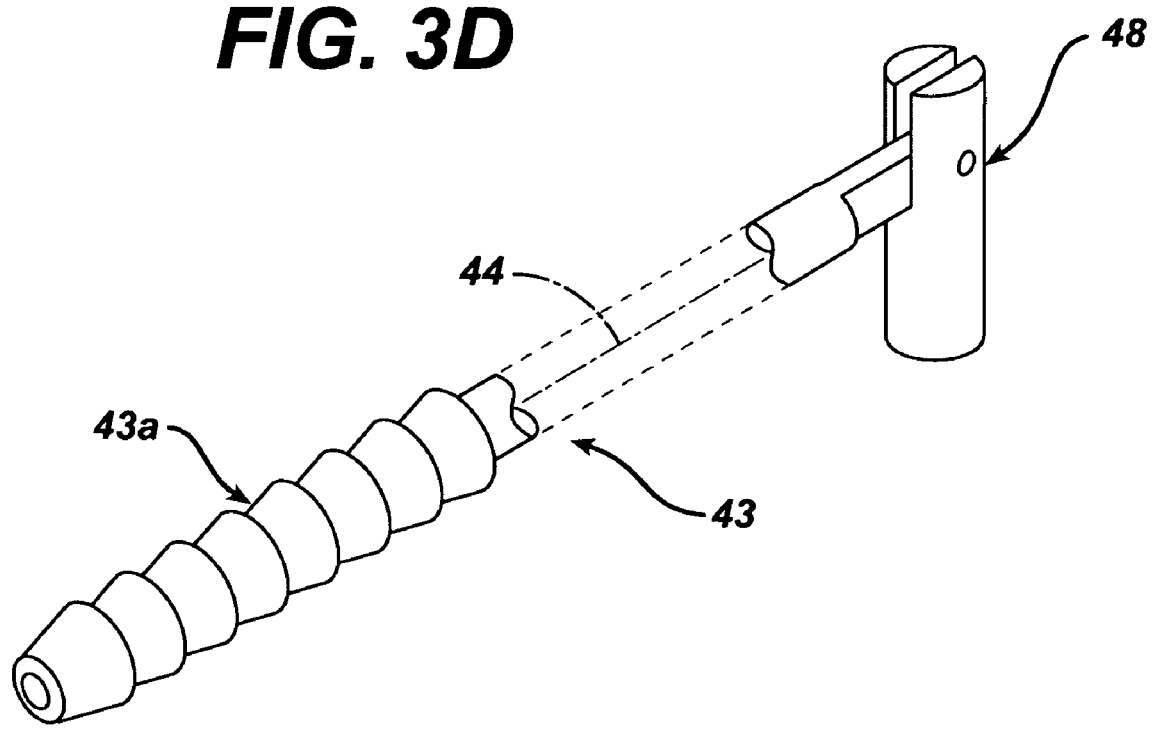
FIG. 3D illustrates an embodiment wherein the first bearing member is a toggle that can rotate to a position perpendicular to the axis of the sternum joining member. Also illustrated is a sternum joining member with a barbed exterior on at least a portion of the axis.

Yet another embodiment is illustrated in FIG. 3D. The first bearing member is a toggle 48 that can rotate to a position perpendicular to the axis 44 of the sternum joining member 43. As a result, the device is easily pushed through the holes placed in the sternum from the anterior surface 18 of the sternum and may then be pulled back to deploy the toggle into the perpendicular configuration. In this embodiment, the sternum joining member 43 is a hollow, flexible shaft with a barbed exterior 43a or circumferential or semi-circumferential ratchets on at least a portion of the axis 44. The barbed surface 43a would only allow movement of the second bearing member in the direction of the first bearing member. The barbed surface 43a may also serve to fix the sternum joining member 43 within the cancellous portion of the sternum.

Figure 3E:
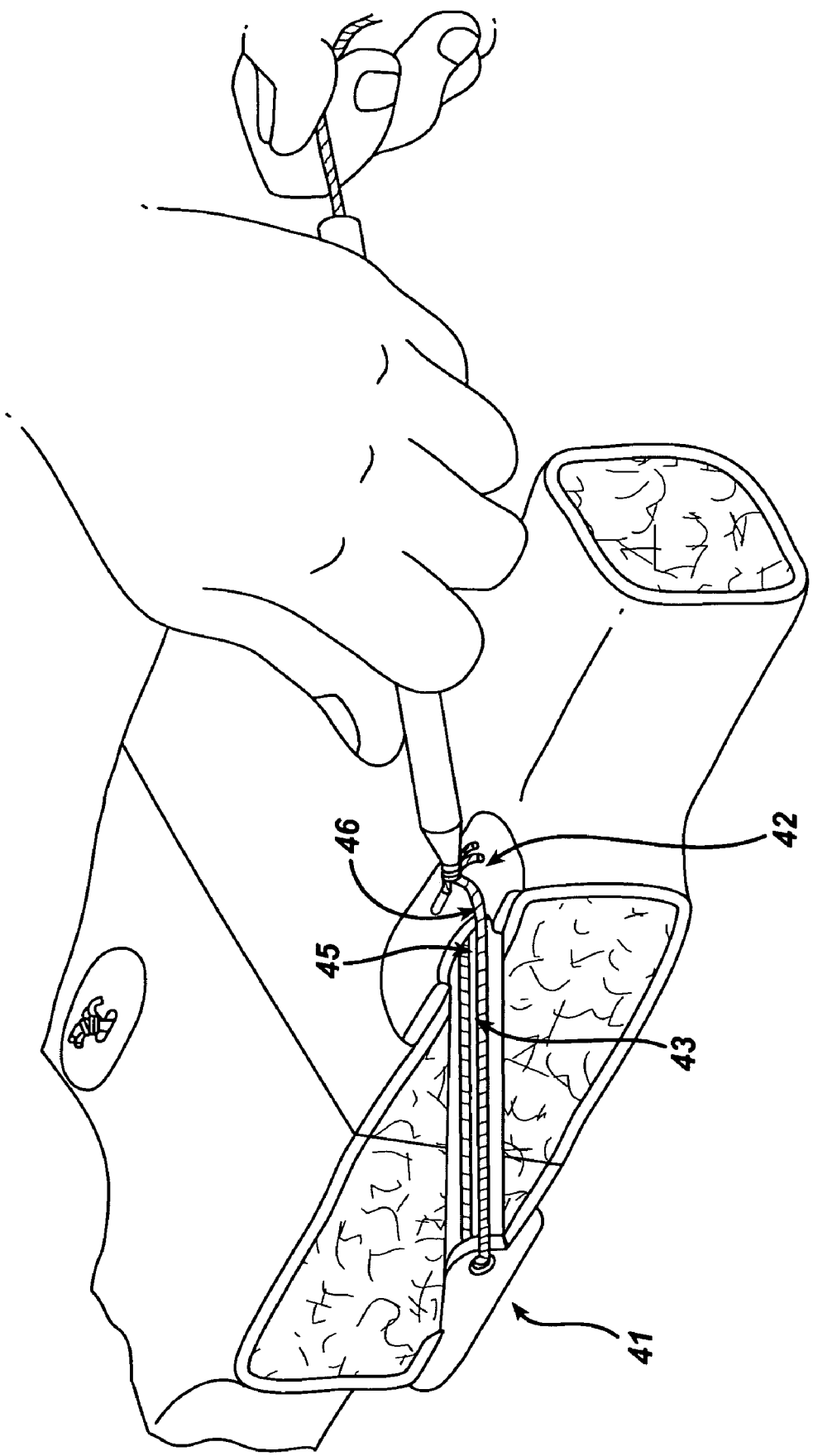
FIG. 3E illustrates another embodiment in which a toggle serves as the first bearing member and the sternum joining member is a surgical suture or stainless steel wire.

FIG. 3E illustrates still yet another embodiment in which a toggle serves as the first bearing member 41. The toggle is pushed through the holes placed in the sternum and then pulled back to act as an anchor against the cortical surface of one of the sternal portions. The sternum joining member 43 may be a surgical suture such as EthiBond™ (Ethicon, Inc.) or stainless steel wire that has a caliber capable of providing enough strength to securely close the sternum. The second bearing member 42 would have means for attaching to second end 46 of the sternum joining member, or may optionally be secured to the second end 46 of the sternum joining member 43 prior to insertion into the sternum. As shown in FIG. 3E, the sternum joining member 43 may optionally be sufficiently long so as to be attached to the second bearing member at its first end 45 and second end 46.

Figure 4:
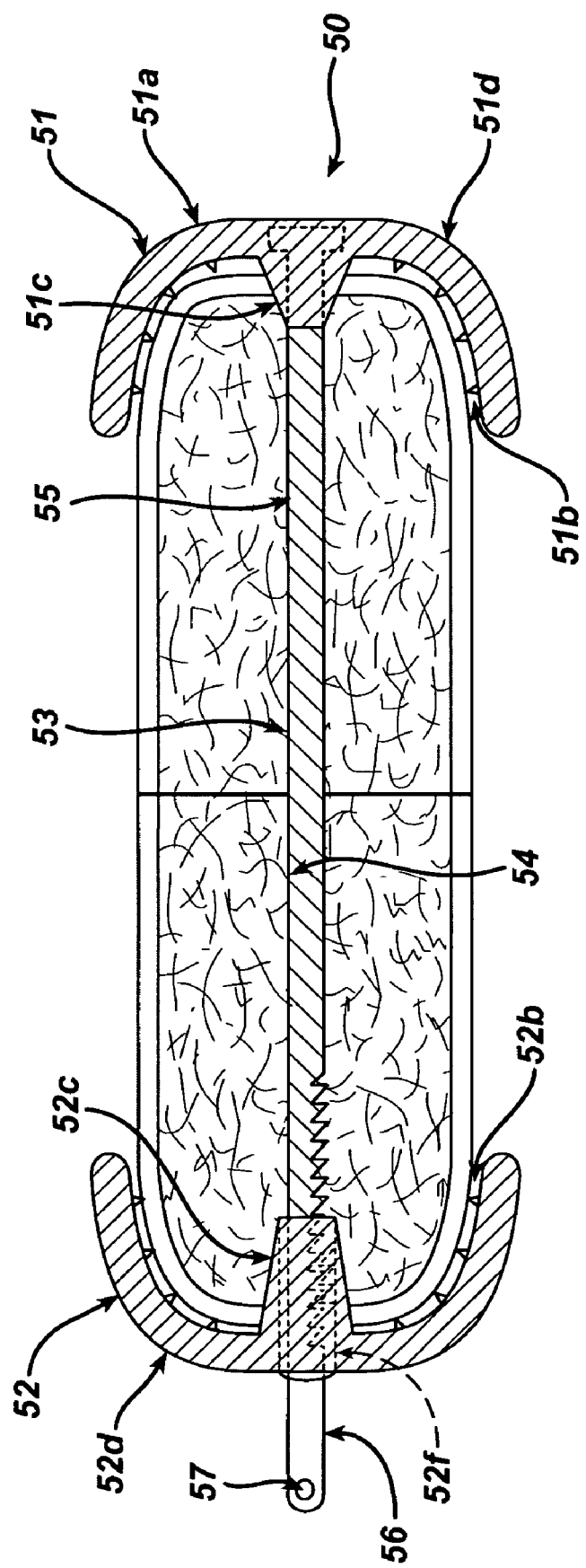
FIG. 4 illustrates a cross-sectional view of an alternative embodiment of the first and second bearing members and how it can be used to close a severed sternum. The sternum is also illustrated in cross-section.

Referring now to FIG. 4, an alternative embodiment of the sternal closure device 50 is shown with substantially C-shaped first bearing member 51 and substantially C-shaped second bearing member 52. The first 51 and second bearing member 52 may be generally C-shape with a sternum contacting side 51b and 52b, optionally a protrusion 51c and 52c that extends away from the sternum contacting side 51b and 51b, and a surface 51d and 52d that faces away from the sternum. As with the device described in FIG. 2, the protrusion 51c and 52c may be inserted into the hole placed in the severed sternum and may have, for example, a lumen 52f that extends through the protrusion 52c on the second bearing member 52. The second bearing member 52 is adapted to be slidably engaged with the axis 54 of the sternum joining member 53 having a first end 55 and a second end 56. The device also may have advancing and/or securing means such as those described above that facilitate movement of the second bearing member 52 towards the first bearing member 51. The second end 56 of the sternum joining member 53 may include a hole 57, a hook, flared end, or indentation that can be used, along with a grasping or hooking device to help draw the second end 56 through the cortical 16 and cancellous surfaces 17 of the sternum 10, such that the axis 54 traverses the sternal incision margins created when the sternum was severed into two portions, in a pathway substantially perpendicular to the sternal incision.

Figure 5:
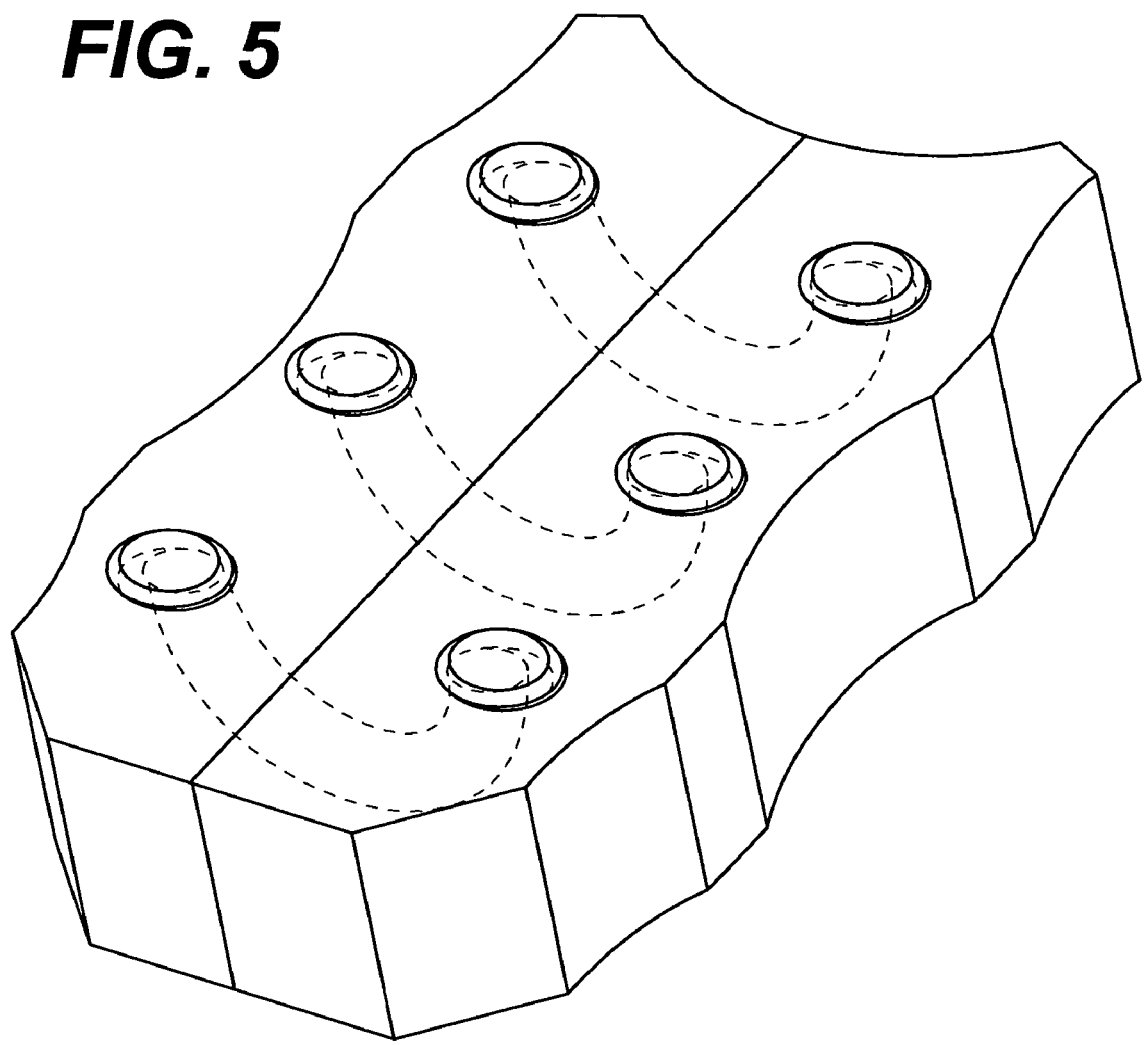
FIG. 5 illustrates an embodiment of the sternal closure device utilizing an arcuate sternum joining member.

Alternatively, as shown in FIG. 5, the sternal closure device may comprise first and second bearing members and a sternum joining member having an arcuate shape and first and second ends; where the first and second ends of the arcuate sternum joining member are connected to the first and second bearing members, which may be in the form of shoulders; and the arcuate sternum joining member is adapted to traverse the cancellous surfaces of the first and second sternal portions in an arcuate pathway.

Figure 6:
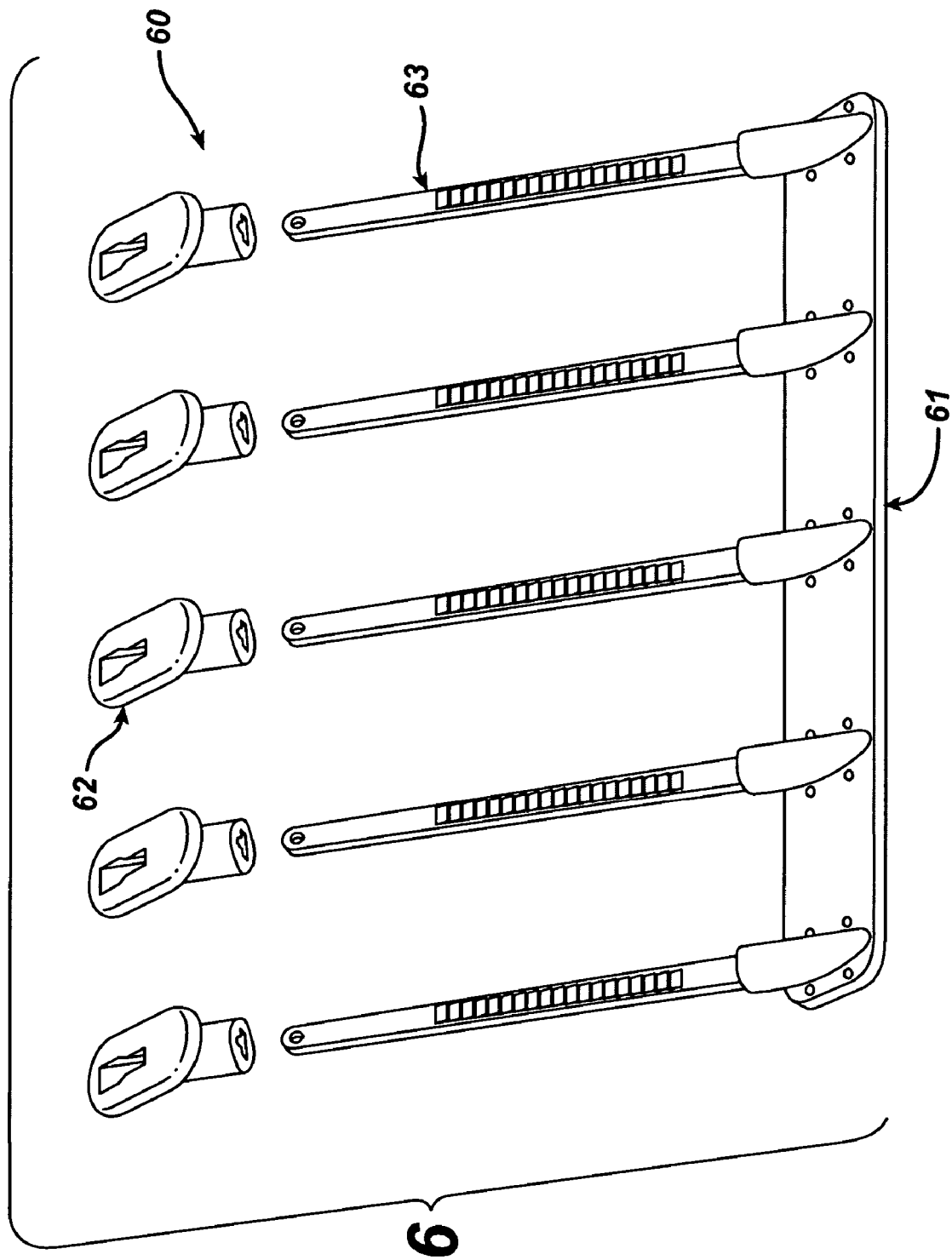
FIG. 6 illustrates an isometric view of an alternative embodiment of the sternal closure device in which a plurality of sternum joining members are linked to one first bearing member.

FIG. 6 illustrates an embodiment 60 in which a plurality of the sternum joining members 63 are linked to a plurality of first bearing members 61 that are connected via a flexible rail or strip. Use of this alternative embodiment may increase the speed at which the sternum can be closed. While each of the second bearing members 62 preferably remain unlinked to each other, it may also be desired to have each of the second bearing members 62 linked by a single rail or strip (not shown).

Preferably, each of the components described in the embodiments discussed thus far in FIGS. 2-6 are comprised of a biocompatible polymer such as polypropylene. Alternatively, the embodiments may be comprised of polymers selected from the group consisting of polytetrafluoroethylene, polyethylene, nylon, or ultra-high molecular weight polyethylene. Resorbable polymers, i.e., those that are removed by the body by way of hydrolysis or enzymatic activity, or combinations thereof may also be used. These polymers may be selected from the group consisting of polylactide (PLA) or polyglycolide (PGA) or copolymers thereof, polyglecaprone, and polydioxanone. In other embodiments, one or more components may be comprised of biocompatible metals such as stainless steel, titanium, nitinol, and other shape memory alloys and superelastic alloys. Antimicrobial agents, analgesic agents, anti-inflammatory agents, hemostatic agents, or agents such as bone morphogenic protein (BMP) or hydroxyapatite that promote bone growth can be incorporated into or coated onto one or more components of the device.

Figure 7:
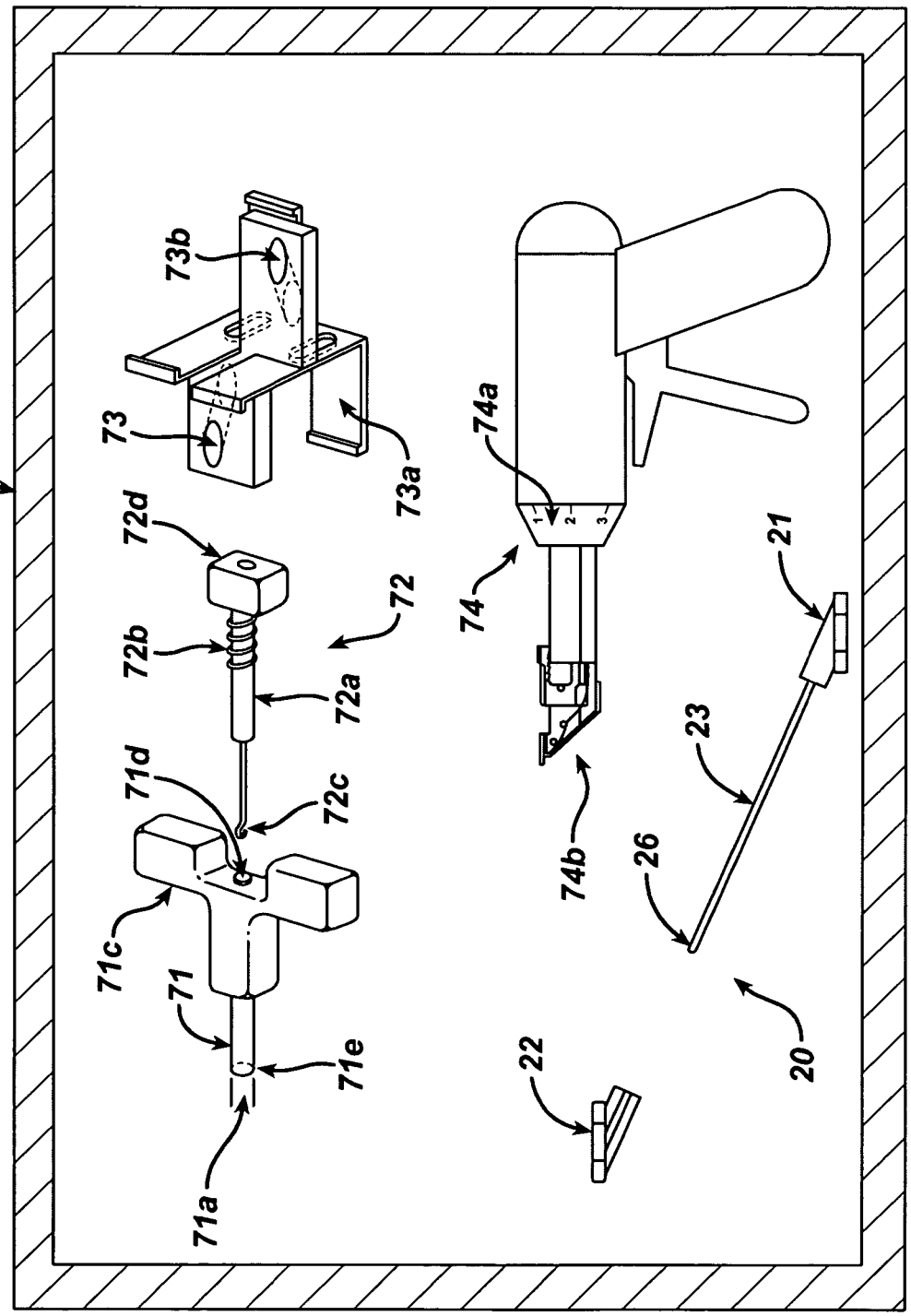
FIG. 7 illustrates a kit containing a plurality of sternal closure devices, a bone punch, a punch guide, a grasping device, and a tensioning tool.

Illustrated in FIG. 7 is a kit 70 for using the sternal closure devices of the present invention. The kit 70 contains at least one of the sternal closure devices illustrated in FIGS. 2-6 and several other instruments or tools that may be optionally used by the surgeon. In this schematic, the sternum closure device of FIG. 2 is illustrated and generally referred to as reference numeral 20. The kit is further comprised of means for creating a hole in the sternum, preferably a bone punch 71 having an internal diameter 71a wide enough to make a hole in the sternum that can receive one of the protrusions on the first bearing member 21 or second bearing member 22. The internal diameter 71a of the bone punch 71 will also be large enough to accommodate passage of the grasping instrument 72 which can be used to pull the second end 26 of the sternum joining member through the sternum. The grasping instrument 72 is comprised of a shaft 72a and preferably has a spring 72b axially disposed on the shaft 72a so that the distal end 72c of the grasping instrument 72 can only be past the distal end 71e of the bone punch 71 when pressure is applied to the proximal end 72d of the grasping instrument 72. The bone punch 71 will preferably have a handle 71c that is easily and safely used by the surgeon. The handle 71c will also have a lumen 71d therein to receive the grasping instrument 72, if necessary.

The kit is further comprised of a punch guide 73 that can be applied to the sternal incision margins or severed edge of the sternal portions so as to provide a means for accurate and reproducible hole sizes, angle, depths, etc. The punch guide has holes 73b drilled in it to serve as the path for the bone punch 71. The punch guide 73 may also have a stop 73a thereon to prevent the bone punch from puncturing or damaging any vital structures, i.e., the depth of the hole created will be limited. The kit is further comprised of a moving means such as a tensioning tool 74 that grabs the second end 26 of the sternum joining member 23 while simultaneously pushing the second bearing member 22 along the axis of the sternum joining member 23 towards the first bearing member 21. The tensioning tool preferably has means 74a for setting the desired tension to be applied to the sternum joining member 23 and means disposed on its distal end 74b for cutting excess portions of the sternum joining member 23 away. The kit may optionally be further comprised of instructions for use.

One method of implanting the sternal closure device of the present invention will now be described in detail. The traditional incision of the sternum involves cutting the sternum with a fine-toothed saw that is applied perpendicular to the plane of the anterior surface of the sternum. After the sternal incision is made, the cancellous surface of each sternal portion is exposed. A retractor is then used to provide sufficient exposure to the organs in the thoracic cavity so that a surgical procedure can be performed therein. After the surgical procedure has been completed, the retractor is removed and the two portions of the severed sternum are now ready to be secured together.

Figure 8:
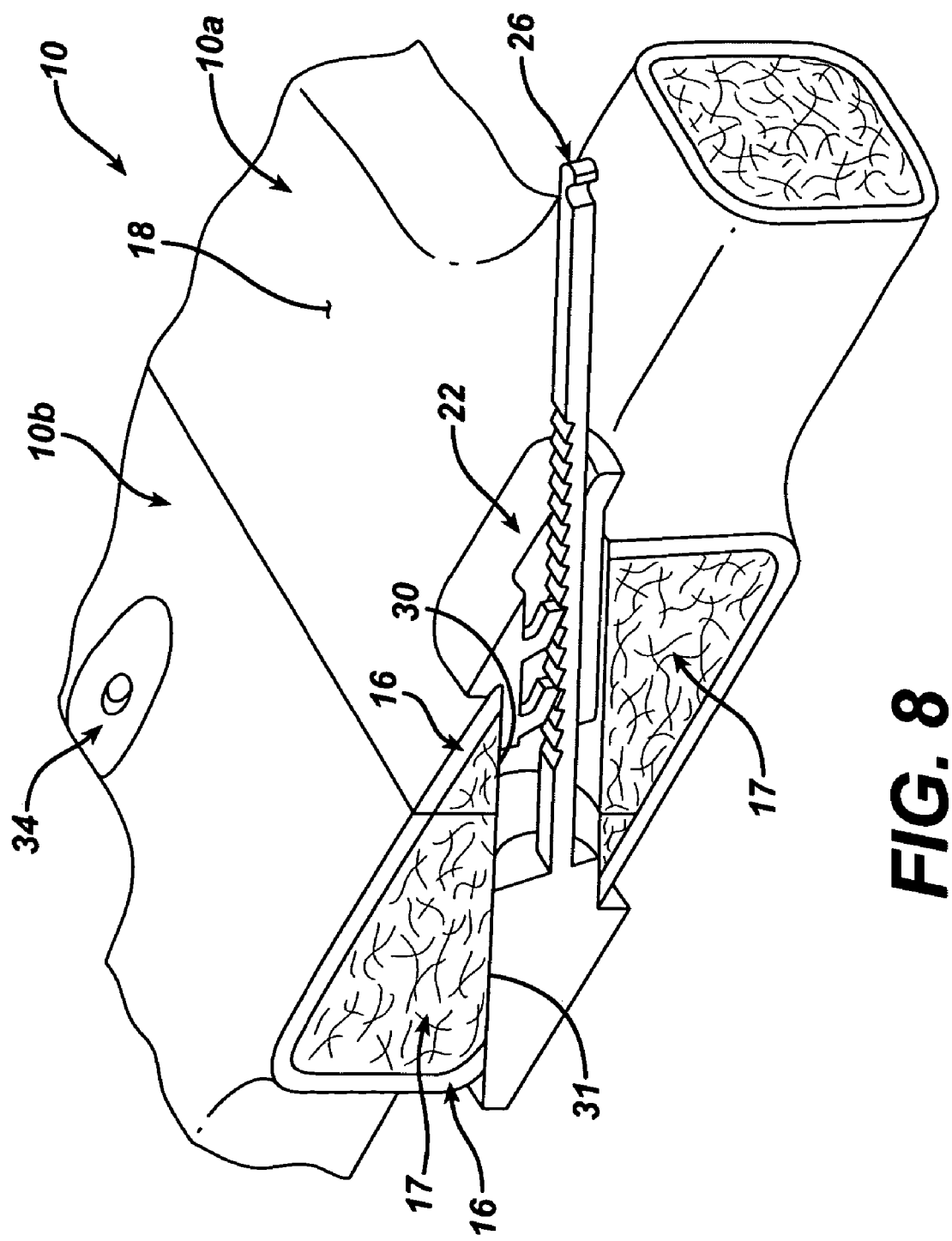
FIG. 8 illustrates a cross-sectional view of the embodiment of FIG. 2 closing two portions of a severed sternum. The sternum is also illustrated in cross-section.

FIG. 8 illustrates a cross-sectional view of the sternal closure device 20 closing a first 10a and second portion 10b of a severed sternum. A punch guide 73 and a bone punch 71 described in FIG. 7 would preferably be used to form holes in the sternum 10 that are oblique with respect to the sternal incision. Alternatively, holes could be made with other surgical tools and instruments such as a needle, trocar, or drill. The holes are preferably made so that an "X" truss like configuration is made, as viewed perpendicular to the plane of the sternal incision. This implantation method will prevent the sternum 10 from being able to potentially rotate around the axis of the incision. Alternatively, a bone punch can be used without a guide 73. The guide 73 allows for deliberate and careful placement of the holes in the sternum and therefore, vital structures such as the internal mammary artery can be identified and avoided. Holes should be made wide enough for the protrusions 21c and 22c on each of the first and second bearing members 21 and 22 to fit into.

As shown in FIG. 8 in conjunction with FIG. 2, protrusion 21c of the first bearing member 21, with or without the sternum joining member 23 engaged therewith, may be inserted into a hole 30 in the first sternal portion 10a to a point where the sternum contacting surface 21b of the first bearing member 21 contacts the cortical surface 16 of the first sternal portion 10a. For example, if the sternum joining member 23 is rigidly engaged with the first bearing member 21, the insertion of the sternum joining member 23 and protrusion 21c of the first bearing member 21 maybe facilitated through the use of a grasping instrument 72 shown in FIG. 7 that is adapted to grab the hole 27 in the second end 26 of the sternum joining member 23, from the anterior surface 18 of the sternum 10. The second end 26 of the sternum joining member 23 is shown after being inserted through a hole 31 placed in the cancellous 17 and cortical surfaces 16 of the second sternal portion 10b, so the axis 24 of the sternum joining member 23 traverses, i.e., passes through, the cancellous surfaces 17 of the first sternal portion 10a and second sternal portion 10b. In FIG. 8 (in conjunction with FIG. 2), the second end 26 of the sternum joining member 23 is shown after being inserted through the lumen 22f of the second bearing member 22. The second bearing member 22 is shown after being slid down the axis 24 of the sternum joining member 23 to a point where the sternum contacting side 22b contacts the second sternal portion 10b. The second bearing member 22 is then continuously advanced onto the axis 24 of the sternum joining member 23 by advancing means such as a tensioning tool 74 that is preferably capable of applying a specified amount of tension. This tensioning tool is also adapted to grab the second end 26 of the sternum joining member 23 while simultaneously pushing the second bearing member 22 towards the first bearing member 21. In this process, the tension in the sternum joining member 23 is increased, thus forcing the two sternal portions 10a and 10b together. Once an appropriate amount of tension is obtained, the advancement of the second bearing member 22 is stopped and the desired tension in the sternum joining member 23 held constant by securing means such as that described in FIG. 2. This enables the sternum joining member 23 to be uniformly tensioned, the tension quantified, and eliminates surgeon variability. The excess second end 26 of the sternum joining member 23 may then be cut off flush with the surface 22d of the second bearing member that faces away from the sternum. Thus, the amount of material remaining that could potentially irritate the patient is reduced. The remaining tissue layers can now be closed by conventional means.

Also illustrated in FIG. 8 is the top surface 34 of another second bearing member that has already been deployed, where the excess portion of the sternum joining member for this sternal closure device has been trimmed away. The first bearing member (not shown) for this device is attached to the second sternal portion 10a. As a result, an "X" type of configuration is obtained for improved sternum is stability, particularly with respect to axial movement of the sternal portions relative to one another. The side 22d of the second bearing member that faces away from the sternum is essentially flush with the cortical surface 16 of the sternum 10.

Alternatively, the method of closing the severed sternum comprises placing holes within the intercostal spaces on each portion of the severed sternum and using the sternal closure device 50 illustrated in FIG. 4 to close the sternum. The sternum joining member 53 traverses the margin of the severed sternum in a path substantially perpendicular to the sternal incision. The surgeon may also choose to use this alternative embodiment shown in FIG. 4 with the embodiment described in FIG. 2. For example, the surgeon may use the embodiment described in FIG. 2 at the manubrium and xiphoid process and the embodiment described in FIG. 4 along the body of the sternum.

The number of devices of the type shown in FIG. 2 that may be required to close a full median sternotomy will range from 2-10, preferably 3-8, with the placement of the sternal closure devices being alternated. In one method, the first end of one sternal closure device would be placed on one sternal portion, and the first end of another sternal closure device would be placed through the opposite sternal portion so that an "X" configuration is repeated along the length of the sternum. The benefits of this device and method of closure can readily be seen. The use of a sternum joining member that traverses the cancellous surfaces of both sternal portions prevents axial movement of one sternal portion relative to the other. The device employs large load bearing surfaces both in the form of protrusions and the sternum contacting side disposed on each bearing member to prevent hole enlargement, such that when the device is utilized as described herein, axial motion of the sternal portions relative to one another is prevented. There is also uniform compression along the length of the severed sternum. The device, particularly the first bearing members and second bearing members, provide a low profile for patient comfort and reduced tissue compression. The device is also simple to apply and safe to use.

It is understood that various modifications and changes in form or detail could readily be made without departing from the spirit of the invention. It is therefore intended that the invention be not limited to the exact forms described and illustrated, but should be constructed to cover all modifications that may fall within the scope of the appended claims. Thus, the device and method could be used to close other bones such as cranial defects, fractures of bones in the skull, vertebral fractures, fractures of in the arms and legs, and fractures of bones in the hands and feet.

We claim:

1. A method for closing a severed sternum having first and second portions that are formed after a sternal incision has been made perpendicular to the plane of the anterior or posterior surface of the sternum, each portion having exposed cortical and cancellous surfaces at the sternal incision margin, comprising: placing at least one first hole in the first sternal portion, such that the first and second holes form a pathway from the anterior surface to the posterior surface of the sternum, the pathway obliquely traversing the sternal incision margins when the first and second sternal portions are approximated; at least partially approximating the first and second sternal portions, and performing one of the following steps (a)-(d):

(a) providing a device comprising a first bearing member having a collapsed and an expanded position, a second bearing member, and a sternum joining member having an axis and engaging the first and second bearing members; inserting the first bearing member through the pathway with the first bearing member in a collapsed position, until the first bearing member extends past the posterior surface of the sternum and assumes the expanded position; moving the second bearing member along the axis of the sternum joining member until the first and second sternal portions are approximated; and securing the sternum joining member to the second bearing member; or (b) providing a device comprising a first bearing member having a collapsed and an expanded position, and a sternum joining member engaging the first bearing member and having an axis and a free end, inserting the first bearing member through the pathway with the first bearing member in a collapsed position, until the first bearing member extends past the posterior surface of the sternum and assumes the expended position; engaging a second bearing member with the free end of the sternum joining member; moving the second bearing member along the axis of the sternum joining member until the first and second sternal portions are approximated; and securing the sternum joining member to the second bearing member; or (c) providing a device comprising a first bearing member, and a sternum joining member engaging the first bearing member and having an axis and a free end; inserting the free end of the sternum joining member in the formed pathway from either the anterior or posterior surface of the sternum until the free end extends past the opposite surface of the sternum; engaging a second bearing member with the free end of the sternum joining member; moving the second bearing member along the axis of the sternum joining member until the first and second sternal portions are approximated; and securing the sternum joining member to the second bearing member; or (d) inserting a sternal joining member having an axis and first and second ends, in the formed pathway until the ends extends past the anterior and posterior surfaces of the sternum; engaging a first bearing member with the first end and a second bearing member with the second end of the sternum joining member; moving the second bearing member along the axis the sternum joining member until the first and second sternal portions are approximated; and securing the sternum joining member to the second bearing member.

2. A method for closing a severed sternum having first and second portions that are formed after a sternal incision has been made perpendicular to the plane of the anterior or posterior surface of the sternum, each portion having exposed cortical and cancellous surfaces at the sternal incision margin, comprising: placing at least one first hole in the first sternal portion and at least one second hole in the second sternal portion, such that the first and second holes form a pathway from one intercostal space in the first sternal portion to an opposite intercostals space in the second sternal portion, the pathway perpendicularly traversing the sternal incision margins when the first and second sternal portions are approximated; at least partially approximating the first and second sternal portions; and performing one of the following steps (a) or (b):

(a) providing a device comprising a first bearing member, and a sternum joining member engaging the first bearing member and having an axis and a free end; inserting the free end of the sternum joining member in the formed pathway from one intercostal space until the free end extends into the opposite intercostal space; engaging a second bearing member with the free end of the sternum joining member; moving the second bearing member along the axis of the sternum joining member until the first and second sternal portions are approximated; and securing the sternum joining member to the second bearing member; or (b) inserting a sternal joining member having an axis and first and second ends, in the formed pathway from one intercostal space until the first and second ends extend into opposite intercostal spaces; engaging a first bearing member with the first end and a second bearing member with the second end of the sternum joining member; moving the second bearing member along the axis of the sternum joining member until the first and second sternal portions are approximated; and securing the sternum joining member to the second bearing member.

* * * * *